(12) United States Patent
Torii

(10) Patent No.: US 11,104,590 B2
(45) Date of Patent: Aug. 31, 2021

(54) STERILIZATION DEVICE USING STRAIGHTENER AND UV LED ARRAY FACING THE STRAIGHTENER

(71) Applicant: NIKKISO CO., LTD., Tokyo (JP)

(72) Inventor: Nobuhiro Torii, Hakusan (JP)

(73) Assignee: Nikkiso Co., Ltd., Tokyo (JP)

( * ) Notice: Subject to any disclaimer, the term of this patent is extended or adjusted under 35 U.S.C. 154(b) by 0 days.

(21) Appl. No.: 15/873,217

(22) Filed: Jan. 17, 2018

(65) Prior Publication Data

US 2018/0155215 A1 Jun. 7, 2018

Related U.S. Application Data

(63) Continuation of application No. PCT/JP2016/075193, filed on Aug. 29, 2016.

(30) Foreign Application Priority Data

Sep. 7, 2015 (JP) .............................. JP2015-176159

(51) Int. Cl.
*C02F 1/32* (2006.01)
*A61L 2/10* (2006.01)

(52) U.S. Cl.
CPC ................ *C02F 1/325* (2013.01); *A61L 2/10* (2013.01); *A61L 2202/122* (2013.01); *C02F 2201/328* (2013.01); *C02F 2201/3222* (2013.01); *C02F 2201/3224* (2013.01);
(Continued)

(58) Field of Classification Search
None
See application file for complete search history.

(56) References Cited

U.S. PATENT DOCUMENTS

| | | | |
|---|---|---|---|
| 5,200,156 A | * | 4/1993 | Wedekamp ............... A61L 2/10 313/493 |
| 5,624,573 A | | 4/1997 | Wiesmann |
| 6,524,447 B1 | | 2/2003 | Carmignani et al. |

(Continued)

FOREIGN PATENT DOCUMENTS

| | | | |
|---|---|---|---|
| CN | 204083993 U | | 1/2015 |
| CN | 110143642 A | * | 8/2019 |

(Continued)

OTHER PUBLICATIONS

Japanese Office Action in application No. 2015-176159 dated Dec. 11, 2018, is attached and its English translation; pp. 1-9.
(Continued)

*Primary Examiner* — James Choi
(74) *Attorney, Agent, or Firm* — Muncy, Geissler, Olds & Lowe, P.C.

(57) ABSTRACT

A sterilization device includes: a processing chamber in which a fluid passing through a straightener flows in a first direction, the straightener being provided at an inlet of the processing chamber; a plurality of light emitting devices arranged in an array on a plane facing the straightener in the first direction, sandwiching the processing chamber, and irradiating the fluid in the processing chamber with ultraviolet light; a light source chamber that houses the plurality of light emitting devices inside; and a discharge path provided to the side of the light source chamber and allowing the fluid passing through the processing chamber to flow in the first direction.

7 Claims, 3 Drawing Sheets

(52) U.S. Cl.
CPC ............... *C02F 2201/3227* (2013.01); *C02F 2201/3228* (2013.01); *C02F 2301/022* (2013.01); *C02F 2303/04* (2013.01)

(56) References Cited

U.S. PATENT DOCUMENTS

| | | | | |
|---|---|---|---|---|
| 2010/0176056 | A1* | 7/2010 | Rozenberg | A61L 2/10 210/636 |
| 2011/0076196 | A1* | 3/2011 | Chittka | C02F 1/325 422/68.1 |
| 2011/0278467 | A1* | 11/2011 | Tanaka | C02F 1/325 250/372 |
| 2015/0114912 | A1* | 4/2015 | Taghipour | C02F 1/325 210/748.11 |
| 2015/0314024 | A1* | 11/2015 | Khan | C02F 1/325 250/435 |
| 2018/0134592 | A1* | 5/2018 | Szczesniak | C02F 1/20 |
| 2018/0244543 | A1* | 8/2018 | Ochi | A61L 2/10 |
| 2019/0011088 | A1* | 1/2019 | Kim | F21K 99/00 |
| 2019/0225509 | A1* | 7/2019 | Dhiman | C02F 1/325 |

FOREIGN PATENT DOCUMENTS

| | | |
|---|---|---|
| DE | 3935941 A1 | 5/1990 |
| JP | H01284358 A | 11/1989 |
| JP | H01284385 A | 11/1989 |
| JP | 4-55353 | 5/1992 |
| JP | 04-055353 U | 5/1992 |
| JP | H0572440 A | 3/1993 |
| JP | 2009138252 A | 6/2009 |
| JP | 2014061483 A | 4/2014 |
| JP | 2014205082 A | 10/2014 |
| JP | 2014233646 A | 12/2014 |
| JP | 2014233712 A | 12/2014 |
| JP | 2016511138 A | 4/2016 |
| WO | WO 2014/115146 A1 | 7/2014 |

OTHER PUBLICATIONS

Chinese Office Action based on corresponding Application No. 201680041070.9 dated Oct. 31, 2019.
Office Action with English Language Translation for corresponding Japanese Patent No. 6530681 dated Feb. 17, 2020.

* cited by examiner

36

STERILIZATION DEVICE USING STRAIGHTENER AND UV LED ARRAY FACING THE STRAIGHTENER

RELATED APPLICATION

Priority is claimed to Japanese Patent Application No. 2015-176159, filed on Sep. 7, 2015, the entire content of which is incorporated herein by reference.

BACKGROUND OF THE INVENTION

1. Field of the Invention

The present invention relates to sterilization devices and, more particularly, to a device that sterilizes a fluid by irradiating the fluid with ultraviolet light.

2. Description of the Related Art

It is known that ultraviolet light has sterilization capability. Devices that radiate ultraviolet light are used for sterilization in medical and food processing fronts. Devices that sterilize a fluid such as water continuously by irradiating the fluid with ultraviolet light are also used. One example of such a sterilization device is a water sterilizer module including a plurality of ultraviolet light emitting devices arranged along a flow path.

It is necessary to increase the irradiation level of ultraviolet light irradiating the fluid in order to enhance the sterilization effect of ultraviolet irradiation. However, an increase in the number of light emitting devices to obtain a suitable sterilization effect leads to an increase in the cost.

SUMMARY OF THE INVENTION

In this background, one illustrative purpose of the present invention is to provide a sterilization device capable of enhancing the sterilization capability with a smaller number of light emitting devices.

A sterilization device according to an embodiment of the present invention comprises: a processing chamber in which a fluid passing through a straightener flows in a first direction, the straightener being provided at an inlet of the processing chamber; and a plurality of light emitting devices arranged in an array on a plane facing the straightener in the first direction, sandwiching the processing chamber, and irradiating the fluid in the processing chamber with ultraviolet light.

According to this embodiment, the fluid straightened by the straightener provided at the inlet to flow in the first direction is irradiated with ultraviolet light in the first direction for sterilization. As a result, the fluid is exposed to the ultraviolet light from the light emitting devices over a period of time in which the fluid passing through the straightener flows in the first direction as far as the vicinity of the plurality of light emitting devices. In essence, the period of time in which the ultraviolet light from a light emitting device exposes the fluid can be extended as compared with a case of arranging a plurality of light emitting devices along the flow path and radiating ultraviolet light perpendicular to the flow of the fluid. Thus, according to the embodiment, the cumulative irradiation level of the ultraviolet irradiating the fluid is increased and the sterilization capability is improved even when a relatively small number of light emitting devices are used.

The sterilization device may further comprise: an optical element that converts the ultraviolet light emitted by the plurality of light emitting devices into a parallel light that travels in the first direction.

The optical element may be a rod lens that extends in a direction in which the plurality of light emitting devices are arranged.

The sterilization device may further comprise a cooling path provided opposite to the processing chamber, sandwiching the plurality of light emitting devices, so as to cool the plurality of light emitting devices. The cooling path may communicate with the processing chamber and may be configured such that at least a portion of the fluid in the processing chamber is discharged outside via the cooling path.

An inner surface of the processing chamber may be made of a fluororesin material that reflects the ultraviolet light emitted by the plurality of light emitting devices.

BRIEF DESCRIPTION OF THE DRAWINGS

Embodiments will now be described by way of examples only, with reference to the accompanying drawings which are meant to be exemplary, not limiting and wherein like elements are numbered alike in several Figures in which.

DETAILED DESCRIPTION OF THE INVENTION

The invention will now be described by reference to the preferred, embodiments. This does not intend to limit the scope of the present invention, but to exemplify the invention.

A detailed description of an embodiment to implement the present invention will be given with reference to the drawings. Like numerals are used in the description to denote like elements and the description is omitted as appropriate.

Figure 1:
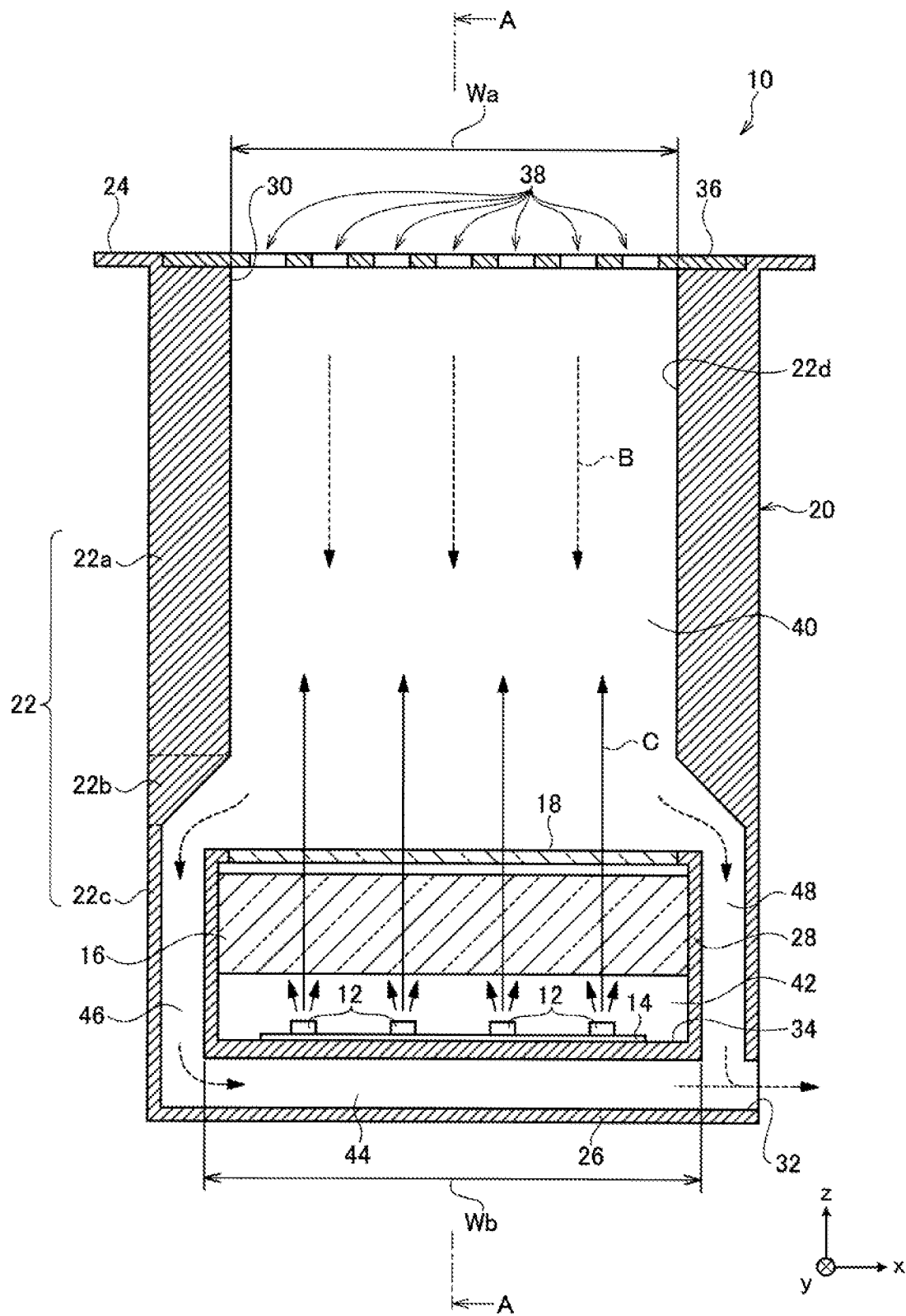
FIG. 1 schematically shows a configuration of a sterilization device according to an embodiment.
Figure 2:
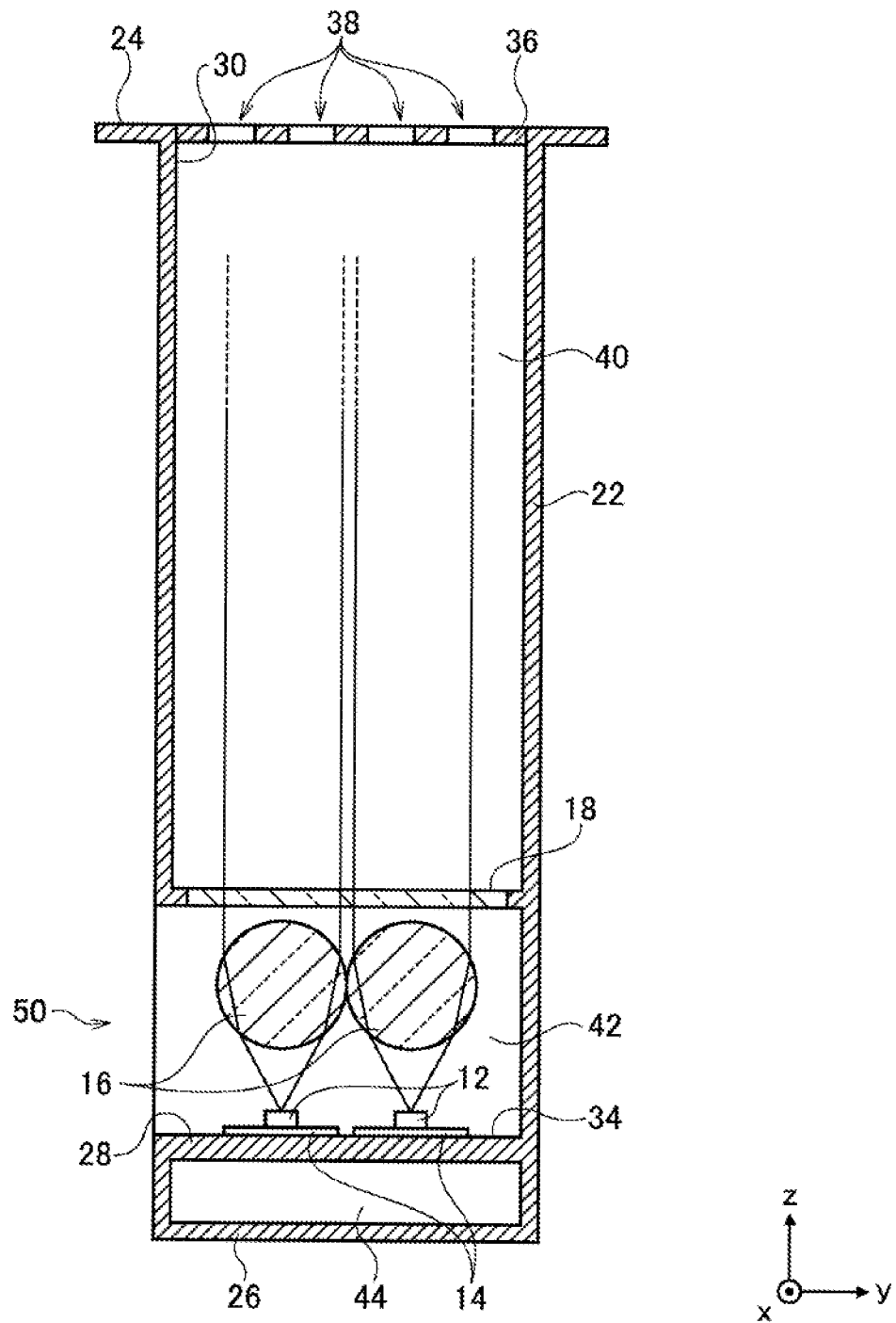
FIG. 2 is a sectional view schematically showing a configuration of the sterilization device of FIG. 1.

FIG. 1 schematically shows a configuration of a sterilization device 10 according to an embodiment and FIG. 2 shows an A-A cross section of FIG. 1. The sterilization device 10 is configured such that a fluid such as potable water is caused to flow into a processing chamber 40 via a straightener 36 at an inlet 30, ultraviolet light is radiated toward the fluid inside the processing chamber 4 from a plurality of light emitting devices 12 so as to sterilize the target fluid. The sterilization device 10 extends a period of time that the fluid flowing in the processing chamber 40 is exposed to ultraviolet light by irradiating the fluid with a ultraviolet light C along a direction B of the flow of the fluid in the processing chamber 40.

The sterilization device 10 includes a plurality of light emitting devices 12, a substrate 14, a rod lens 16, a window part 18, a housing 20, and a straightener 36. Referring to the FIG., x direction and y direction are defined as directions in which the plurality of light emitting devices are arranged, and z direction is defined as a direction perpendicular to both of the x direction and the y direction. The x direction is defined as a direction in which the rod lens 16 extends.

The housing 20 has a shape of a box in which a processing chamber 40, a light source chamber 42, a cooling path 44, a first discharge path 46, and a second discharge path 48 are provided. The housing 20 extends in the first direction (z direction) and an inlet 30 and an outlet 32 are provided at respective ends spaced apart in the z direction. It is desirable that the inner surface of the housing 20 be formed by a member having a high reflectivity for the ultraviolet light emitted by the light emitting devices 12. Preferably, the inner surface 22d is formed by, for example, fluororesin having a high reflectivity for ultraviolet such as polytetrafluoroethylene (PTFE). In this case, the housing 20 may be formed by fluororesin such as PTFE, or the inner surface 22d of the housing 20 may be coated with a liner made of PTFE.

In this specification, the side on which the inlet 30 is provided is referred to as the upstream side and the side on which the outlet 32 is provided is referred to as the downstream side. Inside the housing 20, the processing chamber 40 is provided upstream of the light source chamber 42 and the light source chamber 42 is provided downstream of the processing chamber 40. The light source chamber 42 is surrounded by the processing chamber 40, the cooling path 44, the first discharge path 46, and the second discharge path 48.

The housing 20 includes an outer wall 22, a flange 24, a bottom wall 26, and an inner wall 28. The outer wall 22 includes an upstream wall 22a, a connection wall 22b, and a downstream wall 22c. The upstream wall 22a bounds the circumference of the processing chamber 40 and extends in the z direction along the processing chamber 40. The downstream wall 22c bounds the circumference of the light source chamber 42, the cooling path 44, the first discharge path 46, and the second discharge path 48 and extends in the z direction along the first discharge path 46 or the second discharge path 48. The connection wall 22b is provided between the upstream wall 22a and the downstream wall 22c and bounds the vicinity of the first discharge path 46 and the second discharge path 48.

The inner surface of the upstream wall 22a is formed such that the width Wa of the processing chamber 40 in the x direction is substantially equal to or smaller than the width Wb of the light source chamber 42 in the x direction. Stated otherwise, the upstream wall 22a is formed to be thicker than the connection wall 22b and the downstream wall 22c so that the width Wa of the processing chamber 40 in the x direction is smaller. Meanwhile, inner surface of the downstream wall 22c is formed to be located outward of the light source chamber 42 in the x direction. As a result, the downstream wall 22c is formed to have a thickness smaller than that of the upstream wall 22a. The connection wall 22b is formed such that the thickness thereof in the x direction is progressively smaller downstream and connects the upstream wall 22a and the downstream wall 22c having different thicknesses in the x direction.

The flange 24 is provided at the upstream end of the outer wall 22 and is connected to a pipe, etc. for supplying a fluid processed by the sterilization device 10 to the processing chamber 40. The bottom wall 26 is provided at the downstream end of the side wall 22 and bounds the cooling path 44 along with the inner wall 28. The inner wall 28 is provided to bound the light source chamber 42 along with the window part 18. The inner wall 28 is formed along the cooling path 44, the first discharge path 46, and the second discharge path 48 and provides a partition between the paths and the light source chamber 42.

Inside the light source chamber 42, provided are the plurality of light emitting devices 12, the substrate 14, and the rod lens 16. The light emitting devices 12 are light emitting diodes (LEDs) configured to emit ultraviolet light, and the central wavelength or peak wavelength thereof is included in a range of about 200 nm-350 nm. For example, it is preferable that the light emitting devices 12 be LEDs emitting ultraviolet light near a wavelength range of 260 nm-290 nm having a high sterilizing efficiency. Such ultraviolet LEDs are exemplified by aluminum gallium nitride (AlGaN) based LEDs.

The plurality of light emitting devices 12 are mounted on the substrate 14 and provided on a mounting surface 34 of the light source chamber 42 so as to be oriented to radiate ultraviolet light toward the processing chamber 40 in the z direction. The plurality of light emitting devices 12 are arranged in an array on the mounting surface 34 facing the straightener 36. For example, the light emitting devices 12 are arranged in an array of four light emitting devices in the x direction and two columns in the y direction. The plurality of light emitting devices 12 may be provided to form a linear array including only one column or provided in three or more columns.

The substrate 14 is made by using a highly heat-conductive member. For example, copper (Cu), aluminum (Al), or the like is used as a base material of the substrate 14. The substrate 14 is mounted to the inner wall 28 bounding the cooling path 44 and is cooled by the fluid flowing through the cooling path 44.

The rod lens 16 is provided between the plurality of light emitting devices 12 and the window part 18 so as to extend in the x direction in which the plurality of light emitting devices 12 are arranged. As shown in FIG. 2, the rod lens 16 converts the ultraviolet light from the light emitting devices 12 into a parallel light that travels toward the processing chamber 40 in the z direction. In place of the rod lens 16, a cylindrical lens may be provided as an optical element that turns the light from the light emitting devices 12 into parallel light. Still alternatively, a ball lens or a convex lens associated with each of the light emitting devices 12 may be provided.

The window part 18 provides a partition between the processing chamber 40 and the light source chamber 42 and transmits the ultraviolet light from the light emitting devices 12. The window part 18 is formed of a material having a high transmissivity for the ultraviolet light from the light emitting devices 12. For example, the window part 18 is made of quartz ($SiO_2$), sapphire ($Al_2O_3$), amorphous fluororesin, etc. The window part 18 is fitted to the inner wall 28 so as to prevent the fluid flowing in the processing chamber 40 from entering the light source chamber 42.

As shown in FIG. 2, an opening 50 is provided to the side of the light source chamber 42. The opening 50 provides communication between the interior of the light source chamber 42 and a space outside the housing 20. By providing the opening 50, it is easy to mount the plurality of light emitting devices 12 and the rod lens 16 inside the light source chamber 42. In the event of a failure in some of the plurality of light emitting devices 12, the provision facilitates maintenance to replace the relevant light emitting device 12. A removable cover may be attached to the opening 50.

Figure 3:
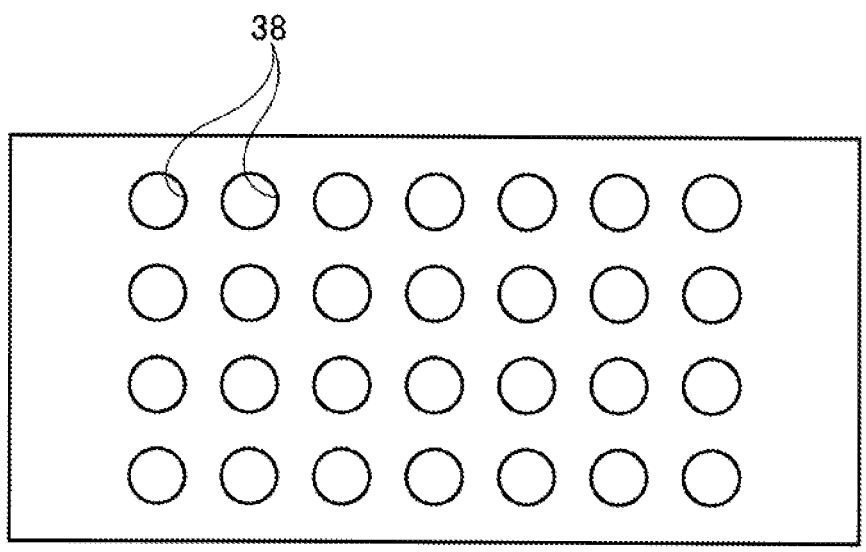
FIG. 3 is an outline view schematically showing a configuration of the straightener.
Figure 3:
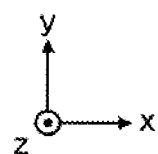

FIG. 3 is an outline view schematically showing a configuration of the straightener 36. The straightener 36 is a porous straightener having a plurality of holes 38 arranged in the x direction and in the y direction. The straightener 36 is provided at the inlet 30 of the housing 20 and straightens the flow of the fluid flowing via the inlet 30. The straightener causes the fluid flowing in the processing chamber 40 to flow in a laminar flow in the z direction. The straightener 36 may not be limited to a porous straightener but may be a straightener mechanism having another shape capable of turning the flow in the processing chamber 40 into a laminar flow.

According to the configuration above, the fluid flowing into the sterilization device 10 is straightened by the straightener 36 and travels in the processing chamber 40 in a laminar flow in the direction B along the z direction. The ultraviolet light C from the light source chamber 42 is turned into a parallel light along the z direction and irradiates the fluid inside the processing chamber 40. A portion of the fluid passing through the processing chamber 40 is discharged from the outlet 32 via the first discharge path 46 and the cooling path 44, and another portion is discharged from the outlet 32 via the second discharge path 48. The fluid flowing in the cooling path 44 cools the light emitting devices 12 that dissipate heat when lighted.

According to this embodiment, the ultraviolet light from the plurality of light emitting devices 12 are propagated in the first direction (z direction) so that not only the fluid in the vicinity of the window part 18 from which the ultraviolet light is emitted but also the fluid near the straightener 36 distanced from the window part 18 is irradiated with high-intensity ultraviolet light. In particular, the fluid flowing into the processing chamber 40 is turned into a laminar flow by the straightener 36 so that the ultraviolet light is propagated farther than when the fluid is turbulent inside the processing chamber 40. This extends a period of time that the fluid is exposed to the ultraviolet light of a predetermined intensity or higher and increases the cumulative irradiation level of the ultraviolet light irradiating the fluid passing through the processing chamber 40.

According to the embodiment, the ultraviolet light from the plurality of light emitting devices 12 is turned into a parallel light so that the ultraviolet light is propagated to the vicinity of the straightener 36 distanced from the window part 18 without attenuating the intensity of the ultraviolet light so much. This increases the cumulative irradiation level of the ultraviolet light to which the fluid is exposed and improves the sterilization capability.

According to the embodiment, the inner surface of the housing 20 is made of a material having a high ultraviolet reflectivity so that the ultraviolet light traveling to the inner surface of the housing 20 is reflected and guided toward the fluid. This increases the cumulative irradiation level of the ultraviolet light to which the fluid is exposed and improves the sterilization capability.

According to the embodiment, by configuring the cross-sectional area of water flow of the processing chamber 40 to be substantially equal to or smaller than the range in which the window part 18 is provided, the entirety of the fluid flowing in the processing chamber 40 is irradiated with the ultraviolet from the plurality of light emitting devices 12. If the width Wa of the processing chamber 40 in the x direction is configured to be larger than the width Wb of the light scarce chamber 42 in the x direction, the fluid flowing along the inner surface of the upstream wall 22a is discharged without being irradiated with ultraviolet light sufficiently. Meanwhile, according to the embodiment, the width of the processing chamber 40 is limited to the range irradiated with the parallel light from the plurality of light emitting devices 12 so that the entirety of the fluid flowing in the processing chamber 40 is suitably irradiated with ultraviolet light.

According to the embodiment, a portion of the fluid flowing in the processing chamber 40 is used to cool the light emitting devices 12 so that the impact such as lower ultraviolet output due to heat dissipation from the light emitting devices 12 or shorter life of the light emitting devices 12 is mitigated.

Described above is an explanation based on an exemplary embodiment. The embodiment is intended to be illustrative only and it will be obvious to those skilled in the art that various modifications to constituting elements and processes could be developed and that such modifications are also within the scope of the present invention.

In one variation, the inventive sterilization device may be used for a purification process that decomposes organic substance included in a fluid by using ultraviolet irradiation.

In another variation, the straightener 36 may not be provided.

It should be understood that the invention is not limited to the above-described embodiment, but may be modified into various forms on the basis of the spirit of the invention. Additionally, the modifications are included in the scope of the invention.

What is claimed is:

1. A sterilization device comprising:
    a processing chamber in which a fluid passing through an inlet, wherein the fluid flows in the processing chamber in a first direction;
    a plurality of light emitting devices arranged in an array on a plane facing the processing chamber in the first direction and irradiating the fluid in the processing chamber with ultraviolet light rays;
    an optical element that converts substantially all of the ultraviolet light rays emitted by the plurality of light emitting devices into parallel light rays that are parallel to the first direction and travels in the first direction;
    a light source chamber that houses the plurality of light emitting devices inside;
    a first discharge path and a second discharge path between which the light source chamber is provided and allowing the fluid passing through the processing chamber to flow in the first direction; and
    a cooling path to cool the plurality of light emitting device, wherein the light source chamber is provided between the processing chamber and the cooling path in the first direction, wherein the fluid passing through the first discharge path flows in the cooling path in a direction perpendicular to the first direction, the fluid passing through the second discharge path merges with the fluid passing through the cooling path in a downstream of the cooling path.

2. The sterilization device according to claim 1, wherein the optical element is a rod lens that extends in a direction in which the plurality of light emitting devices are arranged.

3. The sterilization device according to claim 1, wherein an inner surface of the processing chamber is made of a fluororesin material that reflects the ultraviolet light rays emitted by the plurality of light emitting devices.

4. The sterilization device according to claim 1, further comprising:
    a housing in which the processing chamber, the light source chamber, the first and second discharge paths, and the cooling path are provided, wherein
    the housing includes an upstream wall that bounds the processing chamber, an inner wall that bounds the light source chamber, a downstream wall that bounds the first and second discharge paths along with the inner wall, and a connection wall that connects the upstream wall and the downstream wall, and a thickness of the connection wall in a second direction perpendicular to the first direction is progressively smaller in a direction from the upstream wall toward the downstream wall.

5. The sterilization device according to claim 1, wherein a width of the processing chamber in a second direction perpendicular to the first direction is smaller than a width of the light source chamber in the second direction.

6. The sterilization device according to claim 1, further comprising:
   a straightener provided in the inlet, wherein the fluid path through the straightener in the first direction.

7. The sterilization device according to claim 1, further comprising:
   an outlet in which a first fluid passing through the processing chamber and the first discharge path and a second fluid passing thorough the processing chamber and the second discharge path are merged and then discharged outside.

* * * * *